(12) United States Patent
Granéli et al.

(10) Patent No.: US 8,741,577 B2
(45) Date of Patent: *Jun. 3, 2014

(54) SURFACE IMMOBILISED MULTILAYER STRUCTURE OF VESICLES

(75) Inventors: Annette Granéli, Göteborg (SE); Erik Reimhult, Zurich (CH); Sofia Svedhem, Göteborg (SE); Indriati Pfeiffer, Göteborg (SE); Fredik Höök, Lund (SE)

(73) Assignee: Bio-Rad Laboratories Inc., Hercules, CA (US)

( * ) Notice: Subject to any disclaimer, the term of this patent is extended or adjusted under 35 U.S.C. 154(b) by 1731 days.

This patent is subject to a terminal disclaimer.

(21) Appl. No.: 10/552,649

(22) PCT Filed: Apr. 7, 2004

(86) PCT No.: PCT/SE2004/000555
§ 371 (c)(1), (2), (4) Date: Dec. 4, 2006

(87) PCT Pub. No.: WO2004/090165
PCT Pub. Date: Oct. 21, 2004

(65) Prior Publication Data
US 2007/0116733 A1    May 24, 2007

(30) Foreign Application Priority Data
Apr. 7, 2003 (SE) .................... 0301038

(51) Int. Cl.
*G01N 33/53* (2006.01)
*A61K 9/127* (2006.01)

(52) U.S. Cl.
USPC .......... 435/7.1; 424/423; 424/450; 425/288.1

(58) Field of Classification Search
USPC ............. 424/1.21, 417; 435/6, 458, 287.2; 436/523; 977/907
See application file for complete search history.

(56) References Cited

U.S. PATENT DOCUMENTS

| | | | | |
|---|---|---|---|---|
| 5,922,594 A | * | 7/1999 | Lofås | 435/287.1 |
| 6,235,535 B1 | * | 5/2001 | Keinanen et al. | 436/172 |
| 6,361,944 B1 | * | 3/2002 | Mirkin et al. | 435/6 |
| 2002/0019019 A1 | * | 2/2002 | Hamalainen et al. | 435/7.92 |
| 2005/0079195 A1 | * | 4/2005 | Kataoka et al. | 424/423 |

FOREIGN PATENT DOCUMENTS

| | | | | |
|---|---|---|---|---|
| DE | WO2002081739 | * | 10/2002 | C12Q 1/68 |
| JP | 9-049830 A1 | | 2/1997 | |
| WO | WO0233045 | * | 4/2002 | |
| WO | WO 02081738 A2 | * | 10/2002 | |
| WO | WO 02082078 A2 | * | 10/2002 | |
| WO | WO2004060350 | * | 7/2004 | |

OTHER PUBLICATIONS

Patolsky et al., "Amplified microgravimetric quartz-crystal-microbalance assay of DNA using oligonucleotide-functionalized liposomes or biotinylated liposomes," J. Am. Chem. Soc., 2000, vol. 122, pp. 418-419.*
Patolsky et al., "Electronic transduction of DAN sensing processes on surfaces: amplification of DNA detection and analysis of single-base mismatches by tagged liposomes," J. Am. Chem. Soc., 2001, vol. 123, pp. 5194-5205.*
Mirkin et al., (J.Am. Chem. Soc. 2000,122,6305-6306).*
Zacher et al, "Real-Time Two-Wavelength Surface Plasmon Resonance as a Tool for the Vertical Resolution of Binding Processes in Biosensing Hydrogels", *Langmuir*, 2002, 18, 1748-1759.
Svedhem et al, ChemBioChem, 4:339-343 (2003).
English Translation of Official Action from corresponding JP 2006-508012 mailed Sep. 24, 2009.

* cited by examiner

*Primary Examiner* — Shafiqul Haq
*Assistant Examiner* — Carmencita M Belei
(74) *Attorney, Agent, or Firm* — Porter Wright Morris & Arthur LLP

(57) ABSTRACT

A surface-immobilized multilayer structure of a plurality of vesicles (2), the structure comprising at least one linker (4) immobilized onto the surface, the at least one linker (4) being bound to at least one other linker, which is attached to a vesicle, which optionally may have another linker (5) bound to another linker (5) attached to another vesicle (2), wherein the structure either comprises at least two vesicles (2) bound via linkers (5) to each other or at least two vesicles (2) bound via linkers (5) attached to the vesicles to one linker (4) immobilized onto the surface (1).

33 Claims, 6 Drawing Sheets

SURFACE IMMOBILISED MULTILAYER STRUCTURE OF VESICLES

RELATED APPLICATIONS

This application is a 371 of PCT/SE2004/000555 filed Apr. 7, 2004 and claims priority under 35 U.S.C. §119 to Application Ser. No. 60/461,197 filed Apr. 9, 2003.

TECHNICAL FIELD

This invention relates to:
A surface-immobilised multilayer structure of a plurality of intact vesicles;
Methods and means for producing such multilayer structures;
The use of such multilayer structures in bio-analytical Sensor applications.

TECHNICAL BACKGROUND

There is a strong desire for improved bioanalytical-sensor concepts compatible with detailed analysis of biorecognition events, including, for example, nucleotide-hybridisation, antibody-antigen recognition, drug-receptor interactions etc. In one common approach the analyte molecules (targets) to be recognized by immobilized receptor (probes) are labelled, e.g. with fluorescent or radioactive compounds. In alternative and increasingly important approaches, the biorecognition events are recorded without the introduction of external labels. The demand for label-free detection originates primarily from the observations that: (i) molecules to be detected from complex mixtures are complicated to label 25 in a rapid, reproducible and homogeneous manner, (ii) labels may interfere with the actual biorecognition event and (iii) information from binding kinetics can generally not be achieved, which thus complicates affinity and concentration determinations. Significant progress in this direction has recently been made, thus allowing label-free and sensitive detection of various biorecognition events. Among such analytical methods are optical methods such as SPS/SPR surface plasmon spectroscopy/resonance), (Rich and Myszka 2000) ellipsometry and OWLS (optical waveguide light spectroscopy), (Ramsden 1993) piezoelectric methods such as QCM (quartz crystal microbalance) or SAW (surface acoustic wave) (Janshoff and others 2000) and fluorescent methods such as SPFS (surface plasmon induced fluorescence spectroscopy) (Liebermann and Knoll 2000) and fluorescence imaging (Niemeyer and Blohm 1999). Out of these, SPR is the far most widespread technique (Rich and Myszka 2000. Except for a novel optical design allowing highly sensitive detection of changes in the refractive index at the interface between a gold surface and a liquid, generally an aqueous solution, the technology is compatible with microfluidics for handling of small sample volumes and imaging of patterned surfaces. (Jordan and others 1997) In addition, a variety of gold-surface-modification protocols designed for efficient immobilization of various types of biomolecules have been successfully developed.

However, while the protocols developed for immobilization of water soluble proteins, such as antibodies and many enzymes, as well as oligonucleotides have been proven efficient and reliable, membrane proteins have been shown more cumbersome to handle. This is indeed a severe complication, since supported cell membrane mimics on solid supports aids the fundamental functional studies of e.g. photosynthesis, respiration and neurobiology.

Furthermore, since membrane proteins, especially transmembrane proteins, constitute an important class of proteins, this challenging problem is critical also with respect to pharmaceutical applications, not the least since the majority of drugs are directed towards membrane proteins. The fundamental complication in proper handling of membrane proteins originates from the fact that they, in contrast to water-soluble proteins, carry hydrophobic membrane segments, which must be shielded from water in order for the protein to sustain in its native conformation. This shielding can either be achieved by the use of detergents, which keep the protein soluble in aqueous solution, or preferably by reconstitution of protein into cell-membrane mimicking structures, such as, for example, liposomes or planar supported bilayers. This, in turn, puts strong requirements on the immobilization strategies. In order to develop strategies compatible with immobilization of lipid bilayer assemblies on solid supports, including incorporated membrane proteins, several strategies have been developed. The most straight forward one utilizes spontaneous adsorption, decomposition and fusion of intact vesicles into planar supported bilayers on $SiO_2$, glass or mica-surfaces (Brian and McConnell 1984; Burgess and others 1998; Gizeli and others 1997; Granèli and others 2003; Gritsch and others 1998; Heyse and others 1998; Kalb and Tamm 1992; Lindholm-Sethson 1998; Salafsky and others 1996. However, since the water-soluble parts of membrane proteins incorporated in planar supported bilayers have a tendency to interact directly with the solid support, this strategy has been shown to have a negative influence on the mobility and activity of the protein (Salafsky and others 1996). In addition, the bare presence of the protein may in certain cases interfere with the actual bilayer formation process. (Granèli and others 2003) One promising way to circumvent the former problem is to use a spacer or cushion, often an inert soft polymer, between the protein and the solid support, (Naumann and others 2002; Wagner and Tamm 2000) and EP 07847939; or to create membranes that span small cavities on the surface (Schmidt and others 2000. However, in situations when direct electrical access to both sides of the membrane is 35 not a prerequisite, the use of immobilized intact vesicles may avoid the problems related to the influence from the solid support on the function of the membrane protein, (Cooper and others 2000; Svedhem and others 2003), or the influence from the membrane proteins on the actual bilayer formation process. (Granèli and others 2003) It has been demonstrated how vesicles can be immobilized on a transducer surface utilizing (i) spontaneous binding to a solid support (e.g., Au, $TiO_2$, Pt) (Keller and Kasemo 1998; Reimhult and others 2002), (ii) a fraction of lipids in the vesicles designed to bind specifically to one type of functional entities on a surface (e.g. vesicles containing biotin-modified lipids coupled to streptavidin coated surfaces (Jung and others 2000; Michel and others 2002) or antibody-antigen based coupling (MacKenzie, 1997), (iii) hydrophobic tags immobilized on the transducer surface, (Cooper and others 2000) or (iv) DNA-modified vesicles for specific coupling to DNA modified surfaces, (Patolsky and others 2000) also compatible with array formats. (Svedhem and others 2003)

Furthermore, in comparison with planar supported lipidbilayers, the use of immobilized vesicles enhances the potential number of target sites (e.g. membrane proteins) that can be immobilized per surface area, even in comparison with strategies in which detergent depletion under controlled flow conditions are used to increase the concentration of immobilized membrane proteins in planar supported lipid bilayers. (Karlsson and Lofas 2002; Karlsson and Löfäs 2002) However, it is generally difficult to incorporate membrane proteins with large hydrophilic domains at high concentration in liposomes since the protein then tend to aggregate and lose in activity (see e.g. (Richard and others 1990 and references therein).

Hence, even in situations when immobilized vesicles are used, the surface concentration of proteins must often be kept relatively low. It is therefore of outmost importance to develop strategies where the amount of immobilized membrane protein is increased without significantly influence their function.

DESCRIPTION OF THE INVENTION

The present invention is based on the insight that the above-mentioned problems of a low number of interaction sites between membrane immobilized compounds (probes) and analyte compounds (targets) in solution, generally leads to:
  low signals in biosensor applications, and
  too few sites to produce an efficient filter for molecule fishing, and
  that both of these problems may be solved by increasing the number of surface-immobilized probes capable of binding to such analyte compounds.

Thus, one object of the present invention is to improve the detection sensitivity of analyte-binding and/or release to/from membrane-bound components in sensing applications, utilizing either labelled or label-free detection.

Another object of the present invention is to increase the trapped (or controlled) volume of solution close to a surface, which is realized to be advantageous for a number of applications.

In a first general embodiment the present invention relates to biologically functional surface immobilized multilayer structures comprising a plurality of vesicles sufficiently spaced apart from said surface. The vesicles are directly attached to the structure by surface immobilized linkers with a vesicle-attached (outwardly projecting) linker and optionally by such vesicle-attached linkers to another vesicle. The vesicles comprise the biologically active compounds, which provide the structure with its biological functionality.

In a first aspect, the multilayer structures have vesicles directly attached to the surface immobilized linkers with vesicle-attached linkers in a manner such that two vesicles are attached to each surface immobilized linker. Herein, each vesicle-attached linker is adapted to bind to the surface immobilized linker, but not to another vesicle-attached linker.

In a second aspect, the vesicles are attached to the multilayer structures by the surface immobilized linker and by vesicle attached linkers, so a structure with two or more vesicle layers is provided. Accordingly, the structures will have one layer of vesicles directly linked to surface immobilise linkers and one or several subsequent layers of vesicle-to-vesicle layers formed through links between vesicle attached linkers.

In a second general embodiment, the biologically functional surface immobilized multilayer structure comprising a plurality of vesicles sufficiently spaced apart from the surface, wherein the vesicles are directly attached along surface immobilized linkers with vesicle attached linkers, so at least two vesicles are attached to each linker with vesicle attached linkers. Each vesicle-attached linker is adapted to bind to the surface immobilized linker but not to another vesicle-attached linker. In accordance with this embodiment, the biological functionality may come from a region of the surface immobilized linker that is not attached to the vesicle-attached linkers. Additional or complementary biological functionality may come from compounds comprised by the vesicles attached to the structure.

According to a third embodiment, the presently invented biologically functional surface immobilized multilayer structures, comprising a plurality of vesicles, has vesicles are directly attached to the structure by surface immobilization and by vesicle attached linkers to another vesicle. At least a selected population of the vesicles comprise the biologically active compounds, which provide the structure with its biological functionality. More specifically, biologically active compounds of the vesicles may be impaired or negatively affect in their bioactivity in the vicinity of the surface. Consequently, certain applications it is desirable to let the first, or the layers most close to the surface, be formed of vesicles free from biologically active compounds. Alternatively, all vesicles can comprise biologically active agents. In one aspect of the third embodiment, the surface immobilization of vesicles involves a first population of vesicles adapted for direct surface attachment each having at least one vesicle-attached linker capable of binding to another vesicle-attached linker, in order to construe a multilayer structure. Direct surface attachment of lipid vesicles is a well-established technique to those skilled in the art. One suitable way to accomplish such attachment is to employ hydrophobic surface tags immobilized to the surface as outlined by Cooper and others (2000).

The present invention also relates to methods for producing a surface-immobilised multilayer structure of a plurality of vesicles, the structure itself and the use of such structures in bio-sensing, delivery and filtering applications.

More specifically, the multilayer structure forming method comprises the steps of:
  (i) providing a surface comprising either, at least one linker immobilised onto the surface, said surface-immobilised linker(s) being adapted and available for binding to at least one vesicle-attached linker, or a first layer of directly surface-immobilised vesicles each provided with one or more vesicle-attached linkers;
  (ii) providing vesicles, each comprising at least one outwardly projecting linker attached thereto, said vesicle-attached linker being adapted and available for direct binding to a surface-immobilised linker or another vesicle-attached linker,
  (iii) incubating at least one of the vesicles with the surface under conditions promoting binding of the vesicle-attached linker(s) directly to the surface-immobilised linker(s) or to vesicle-attached linker(s) already immobilised into the structure, resulting in
  (iv) immobilisation of the vesicle(s) and the linker(s) attached thereto into the structure, which after this step comprises at least one structure-immobilised linker and/or surface-immobilised linker available for binding to another vesicle-attached linker (5), and
  (v) repeating the previous step or the previous two steps until the desired amount of vesicles (2) are immobilised into said structure;

In one embodiment of the inventive method (as shown in FIG. 1), several linkers (surface linkers) which are adapted and available for binding to at least two other linkers are immobilised on a surface. At least one outwardly projecting vesicle attached linker (vesicle linkers), adapted and available for binding another linker (vesicle linker or surface linker), are attached to each vesicle. Said vesicles and said surface are incubated together, under conditions at which vesicle attached linkers directly bind to surface-immobilised linkers, upon which the vesicles become immobilised to said surface-immobilised linkers and thus also to said surface. Several vesicles can be immobilised in one step, since the surface-immobilised linkers may be adapted to bind vesicles with different attached linkers to different parts.

In another embodiment of the inventive method (FIG. 2), at least one linker (surface linker) which is adapted and available for binding to another linker is immobilised on a surface. At least one outwardly projecting vesicle attached linker (vesicle linker), adapted and available for binding another linker (vesicle linker or surface linker), is attached to each vesicle. Said vesicles and said surface are incubated together, under conditions at which vesicle linkers can bind to surface linkers, upon binding the vesicles become immobilised to said surface linkers and thus also to said surface as a first layer of vesicles on the surface. The procedure can be repeated, and new vesicles can be incubated together with the surface, under conditions promoting binding of the new vesicles, linkers to linkers attached to vesicles already immobilised to said surface, thus forming subsequent layers of immobilised vesicles on said surface.

In a further embodiment of the inventive method, a first layer of vesicles is directly attached to surface with conventional methods. Such first layer vesicles may be adapted or functionalised to surface attachment, or alternatively, the surface will be adapted with hydrophobic tags. If the neighbouring surface is considered to impair or negatively affect, the biological compounds comprised in the vesicles to render the structure its biofunctionality, first layer vesicles may in one aspect of this embodiment constitute a first population of vesicles without any biological compounds. According to this aspect following layers will comprise vesicles comprising biological agents. The subsequent layers of vesicles will be formed by vesicle-attached linkers as explained above.

In some embodiments of the invention, biologically or in other way chemically active compounds are associated with the lipid bilayer of the vesicles. It may, for example be a naturally occurring or synthetic protein, polypeptide or peptide; it may be a carbohydrate; it may be a designed lipid; it may be a cell-surface protein, such as a cell-surface protein that is characteristic of a particular cell or tissue type, or the surface protein of a pathogen, a tumour cell, or a vitally cell or the like. The vesicle may also have been produced by a cell or the like.

In other embodiments of the invention dyes, drugs or other biologically or in other way chemically active compounds are contained in the interior volume of the immobilized vesicles.

In further preferred embodiments, the surface-immobilized multilayer structure of a plurality of vesicles is adapted for use in a biosensor, where:
  The forming of the multilayer structure is monitored and/or
  Where interactions between said associated biologically active compounds and/or analytes are studied.

In still further preferred embodiments, interactions between said biologically active compounds, coupled either to the membrane or the interior of the vesicles, and analytes, are studied using said biosensors.

In other embodiments of the invention the surface-immobilised multilayer structure of a plurality of vesicles is adapted for use in drug delivery or other forms of controlled release, e.g. in bioinformatics, where said released compounds may or may not react with other immobilized vesicles.

In other embodiments of the invention, the surface-immobilised multilayer structure of a plurality of vesicles is adapted for removing or extracting compounds from a complex solution.

Structures according to the invention have the advantage of providing a significantly higher number of immobilised probe molecules than that of a single lipid bilayer or a single layer of intact vesicles. By building structure with 3-dimensional extension, as opposed to the previously proposed essentially 2-dimensional, structures, the detection capacities of the instruments are better utilised: A larger number of immobilized active compounds leads to the enabling of higher numbers of analyte molecules interacting with the biologically active compounds within the field sensed by a biosensor. The higher the number of such interactions within the sensed field, the better the resolutions of the measurements which thus enable weaker interactions to be detected and enables detection of biologically active compounds and analytes of low molecular weight.

The connection between vesicles and between vesicles and the surface could preferably be mediated through sequence specific hybridisation between oligo- or polynucleotides of DNA and RNA as well as of PNA or other so called DNA-analogues. In comparison with previous strategies by which multilayers of vesicles have been created utilizing biotin-modified lipid vesicles using which multilayers of immobilized vesicles can be formed via intermediate layers of streptavidin (Zacher and Wischerhoff 2002), the oligonucleotides utilized in the present invention can act as efficient spacers, which length easily can be controlled by the design of the oligonucleotides.

A sequence-specific connection strategy opens up the opportunity for site-specific formation of different structures according to the invention. Different oligonucleotides can be attached to different vesicles, which in turn can be incorporated with different biologically active compounds. By immobilising different oligonucleotides on different locations on a surface, separate multilayer structures with different functions can be prepared on the same surface. Also, different vesicles can be immobilized on different locations on relatively long immobilized single stranded oligonucleotides.

In the multilayers of vesicles produced according to the invention, the distance from the underlying support increases per layer, which thus further reduces any obstruction due to the surface on the activity of the compounds immobilized in the vesicles, as well as the permeability of molecules entrapped within the vesicles. The inventive structures are also relatively stable and easy to produce and could easily be tailor made for specific purposes and analysis instrumentations.

DEFINITION OF TERMS

To facilitate an understanding of the present invention, a number of terms are defined below.

As used herein, the term "vesicle" or "liposome" typically refer to essentially spherical structures (5 nm to 20 μm in diameter) built up by lipid membranes, which may or may not contain proteins, glycolipids, steroids or other membrane-associated components.

The terms "liposome" and "vesicle" are used interchangeable herein. Vesicles can be naturally (e g the vesicles present in the cytoplasm of cells that transport molecules and partition specific cellular functions) or synthetically (e g liposomes) generated. The term "vesicle" is here also used for "micelles" which are particles comprising lipids, which particles have a hydrophilic exterior and a hydrophobic interior.

As used herein, the term "nucleotide" refers to any nucleic acid, such as DNA and RNA, as well of nucleic acid analogues such as, but not limited to, PNA (Peptide Nucleic Acid), LNA (Locked Nucleic Acid) and morpholino nucleic acid analogues. The term also relates to any nucleotide comprising the known base analogues of DNA and RNA.

As used herein the term "oligonucleotide" refers to a short length of single-stranded polynucleotide chain. Oligonucleotides are typically less than 100 residues long, however, as used herein, the term is also intended to encompass longer polynucleotides. The term refers to all combinations of nucleotides as defined above, forming a polymer of nucleotides.

As used herein, the term "hybridisation" is used in reference to the pairing of essentially complementary nucleic acids often referred to as Watson-Crick-hybridisation as well as the hybridisation referred to as Hoogsteen-hybridisation.

As used herein, the term "immobilisation" refers to the attachment or entrapment, either chemically or otherwise, of material to a transducer surface in a manner that confines, but not necessarily restricts, the movement of the material.

As used herein, the term "analyte or analytes" refers to any material that is to be analysed.

As used herein, the term "biosensors" refers to any sensor device that is partially or entirely composed of biological molecules. In a traditional sense, the term refers to "an analytical tool or system consisting of an immobilised biological material (such as enzyme, antibody, whole cell, organelle, or a combination thereof) in intimate contact with a suitable transducer device which will convert the biochemical signal into a quantifiable electrical signal" (Gronow 1984).

As used herein, the term "multilayer" refers to structures comprised of at least a second layer formed on top of a first layer. The individual layers may or may not interact with one another.

As used herein, the term "biologically active compound" refers to biological compounds that are capable of interacting with other material or compounds. Such biologically active compounds can include, but are not limited to, proteins, antibodies, nucleotides, lipids, carbohydrates and combinations thereof.

As used herein, the term "membrane protein" refers to proteins or polypeptides, which are connected to or inserted in a lipid bilayer. Such membrane proteins comprise transmembrane proteins as well as proteins with parts embedded in a lipid layer.

As used herein, the term "outwardly projecting compound" refers to a compound with a part that is projecting out from a surface. In the case where the surface is a essentially spherical one, as in the case with vesicles, the term means that the compounds projects from the surface towards the surrounding environment.

As used herein, the term "surface" shall be used in its widest sense. It encompasses all compounds that can be used as support means on which structures can be immobilised.

As used herein, the term "linker adapted for binding" refers to that the linker comprises a compound with ability to bind to another compound.

As used herein, the term "linker available for binding" refers to the situation where a linker is adapted for binding but that the linker is not yet bound to another linker, or all binding sites of the linker are not yet occupied.

BRIEF DESCRIPTION OF THE FIGURES

Preferred embodiments of the invention will now be further described with reference to the accompanying drawings in which.

DETAILED DESCRIPTION OF THE INVENTION

Figure 1:
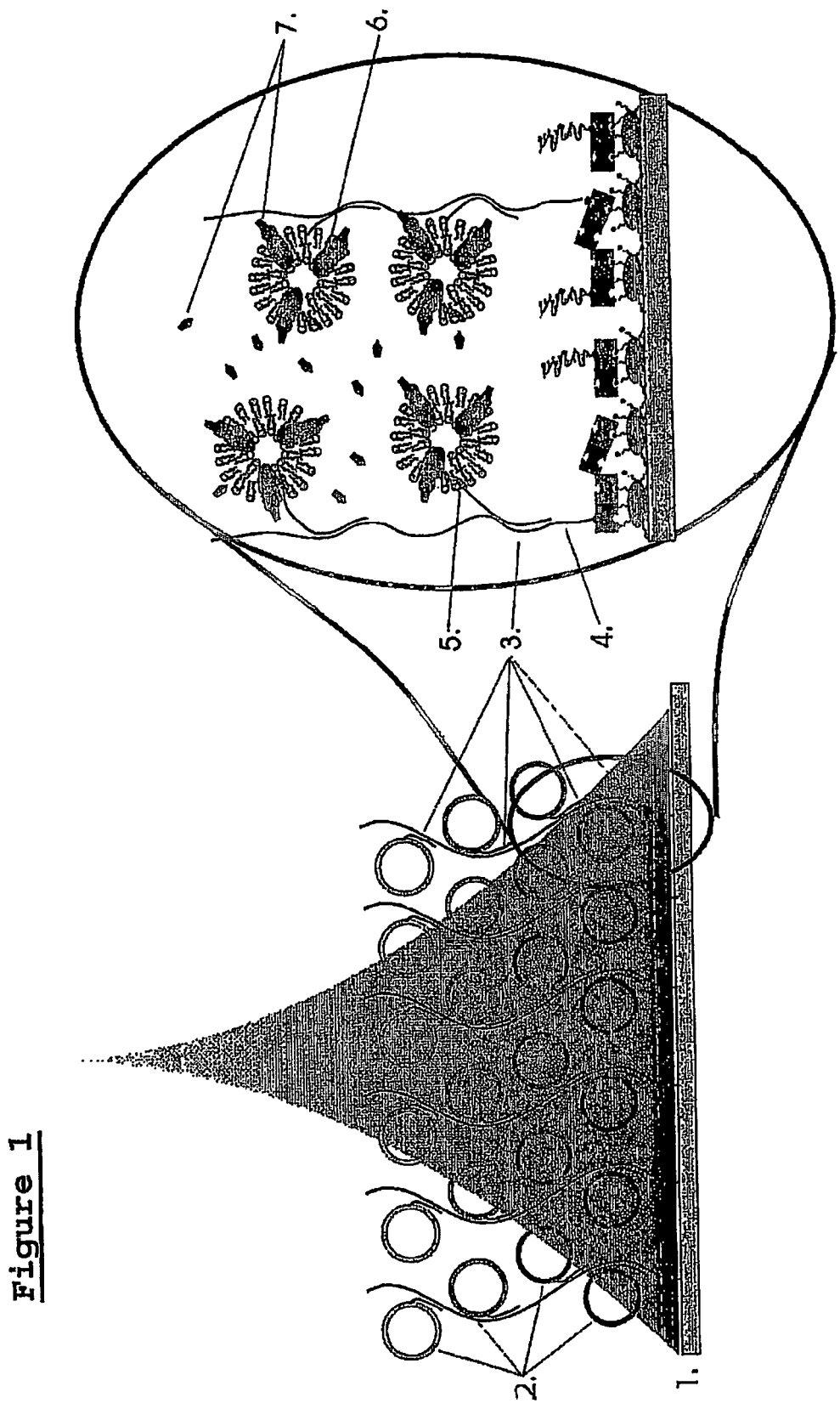
FIG. 1 illustrates an embodiment, in which a plurality of vesicles 2 coupled to a three-dimensional matrix is formed through binding 3 of identical or different linkers 5 attached to different or identical vesicles 2, to identical or different linkers 4 immobilised on a surface 1. The vesicles also comprise biologically active compounds 6 embedded in the lipid bilayer forming the vesicles, and the surrounding environment comprises analytes 7 optionally specific for binding to the biologically active compounds 6.

In preferred embodiments of the invention, the linkers 4 immobilised on the surface 1 as well as the outwardly projecting linkers 5 attached to vesicles 2 comprise oligonucleotides. At least one oligonucleotide is incorporated in each vesicle 2 forming the multilayer structure and the binding 3 of adjacent vesicles 2 to each other as well as the immobilisation of vesicles 2 to the surface 1 is mediated through oligonucleotides.

In other embodiments, the linkers 4, 5 may comprise other compounds or regions with ability of specific binding to a counterpart, so as to complement or extend the biological functionality of the inventive structures. Examples of such compounds can be, but are not limited to pairs of proteins with affinity for each other and pairs of antibodies and antigens.

In preferred embodiments of the invention; outwardly projecting oligonucleotides typically having a length of 1 to 1000 bases are attached to the vesicles 2.

In a preferred embodiment of the present invention, the oligonucleotides are attached to the vesicles 2 via incorporation of an oligonucleotide with one or more hydrophobic anchoring moieties attached to one end of the oligonucleotide as described in WO02/33045 A2. The hydrophobic anchoring moiety incorporates itself, at least partly, into the hydrophobic part of the lipid layer of the vesicle 2, thus anchoring the oligonucleotide in the vesicle with the hydrophilic part of the oligonucleotide projecting outwards from the vesicle 2. The hydrophobic anchoring moiety may comprise compounds that belong to, but is not limited to, the group consisting of cholesterol, fatty acids, hydrophobic peptides and lipids.

In other embodiments, Said oligonucleotides are bound to the vesicle 2, via a reactive group attached to one end of the oligonucleotide to a vesicle 2. The reactive group binds to the lipid head groups of the vesicle. Examples of such covalent bindings are described and referenced to in EP 0784793 and (Patolsky and others 2000). The incorporation of outwardly projecting oligonucleotides may be performed with many different methods. The above-mentioned methods for the incorporation of oligonucleotides into vesicles, as well as other methods not listed here, may be used.

In general, any surface 1 that can be functionalised with oligonucleotides (surface with immobilised oligonucleotides), with one layer of lipid vesicles or with one planar supported bilayer can be used in the invention (i.e. metal surface, polymeric surface, a porous oxide, a semiconductor, glass surface, silica surface, a lipid structure or crystal surface, such as quartz and protein crystals etc). However, the choice of surface 1 is dependent on the final area of use for the invention. In addition, the method for immobilising oligonucleotides to the surface 1 is dependent on the choice of surface. An oligonucleotide functionalised surface could be a surface 1 with oligonucleotides immobilised via affinity (such as, but not limited to, immobilisation of biotinylated oligonucleotides via surface immobilised streptavidin) or via covalent bonds (such as but not limited to, thiol-immobilisation of oligonucleotides to gold surface or silane-immobilisation of oligonucleotides to silica surface).

An oligonucleotide functionalised surface could also be a surface 1 with an immobilised layer of lipids such as, but not limited to, the methods described in EP 0784793, (Cooper and others 2000; Jung and others 2000; Keller and Kasemo 1998; MacKenzie and others 1997; Michel and others 2002; Patolsky and others 2000; Reimhult and others 2002; Svedhem and others 2003) and where outwardly projecting oligonucleotides are incorporated in the layer of lipids or vesicles respectively, and where said oligonucleotides are available for hybridisation.

In a preferred embodiment of the invention, the surface 1 is a metal, for example, but not limited to, gold and silver, functionalised by immobilisation of biotinylated oligonucleotides via surface-immobilised streptavidin.

In a preferred embodiment of the invention, the linkers 4 immobilised on the surface before the immobilisation of vesicles 2 to the surface 1, forms a three dimensional matrix comprising of several different oligonucleotides, typically having a length in the range of 1 to 100 bases, and being complementary to the oligonucleotides on the vesicles 2. The vesicles 2 are immobilised to the matrix via hybridisation of the vesicle-attached oligonucleotides to the matrix comprised oligonucleotides complementary to the vesicle oligonucleotides.

In the embodiment shown in FIG. 1 of the invention, the three-dimensional matrix is composed of long surface-immobilized oligonucleotide strands 4 typically having a length of 100 to 10000 bases, with two or more sequence stretches complimentary to the oligonucleotides on the vesicles 2. The vesicles are immobilised to the surface 1 via hybridisation of the vesicle-attached oligonucleotides 5 to the surface-immobilised oligonucleotides 4 at the stretches 3 complementary to the vesicle oligonucleotides 5. Different vesicles with different oligonucleotides attached to them can hybridise at different sequence stretches on the surface-immobilised oligonucleotides, which implies that the formation of the multilayer structure may be controlled by incubation of different vesicles with different oligonucleotides in separate or parallel steps.

Figure 2:
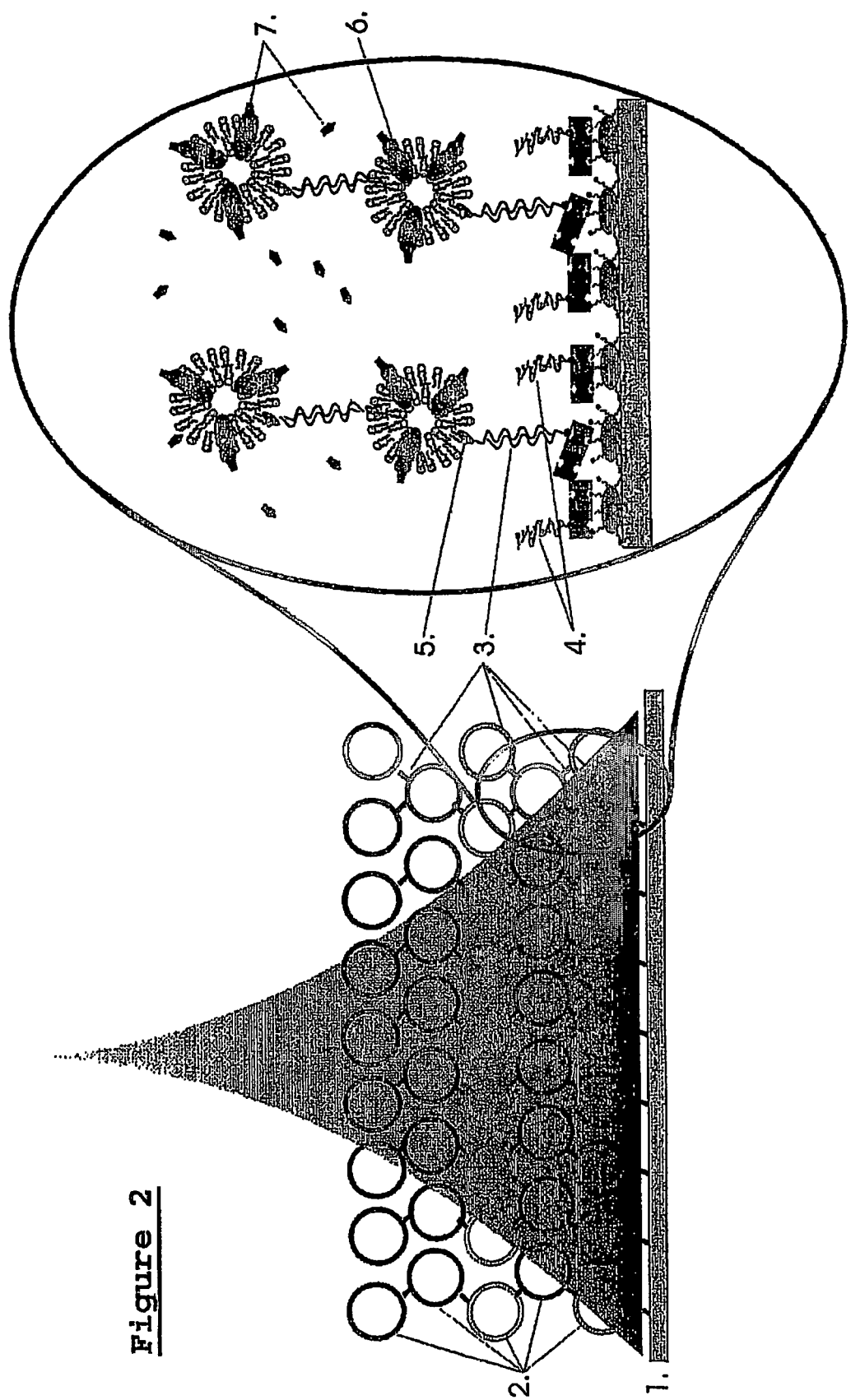
FIG. 2 illustrates an embodiment in which a multilayer of vesicles 2 is formed through binding of vesicle attached outwardly projecting linkers 5 to linkers 4 immobilised on a surface 1. Other linkers attached to the immobilized vesicles are further used to immobilise a second layer of vesicles via linkers 5 attached so said second layer of vesicles. A multilayer is produced by repeating these steps. The vesicles also comprise biologically active compounds 6 embedded in the lipid bilayer forming the vesicles, and the surrounding environment comprises analytes 7 optionally specific for binding to the biologically active compounds 6.

In the embodiment shown in FIG. 2, the linkers 4 immobilised on the surface 1 before the immobilisation of the vesicles 2 comprises of oligonucleotides, typically having a length of 1 to 10000 bases, with one sequence stretch complementary to the oligonucleotides attached to vesicles. Each vesicle forming a first immobilised layer of vesicles on the surface are immobilised via hybridisation of at least one vesicle-attached oligonucleotide to a surface-immobilised oligonucleotide. The vesicles 2 forming a second immobilised layer of vesicles are immobilised on the surface 1 via hybridisation of at least one vesicle-attached oligonucleotide 5 to an oligonucleotide available for hybridisation, and attached to a vesicle comprised in the first immobilised layer. The vesicles forming a third layer of vesicles are in the same way immobilised on the second layer of vesicles. The sequences of the oligonucleotides used for incorporation in vesicles 2, as well as the oligonucleotides immobilised on the surface 1 are chosen in a way that the multilayer structure of choice can be formed.

In the embodiment illustrated in FIG. 1, the oligonucleotides incorporated in the vesicles 2 hybridises with the surface-immobilised oligonucleotides. This implies that the oligonucleotides incorporated in vesicles forming a certain layer of vesicles should have a sequence that enables specific hybridisation to a certain region of the surface-immobilised oligonucleotide located at a certain distance from the surface 1.

In the embodiment illustrated in FIG. 2, the oligonucleotides incorporated in the vesicles 2 forming the first layer hybridises to the oligonucleotides of the modified surface 1, which implies that the sequence of said incorporated oligonucleotides should be chosen in a way so that specific hybridisation between the "first layer"—oligonucleotides and the surface-immobilised oligonucleotides is enabled. Further, the oligonucleotides incorporated in the vesicles 2 forming the second layer hybridises to the oligonucleotides forming the first layer, which means that the sequence of these "second layer"—oligonucleotides should be chosen in a way so that specific hybridisation between said "second layer"—oligonucleotides and said "first layer"-oligonucleotides is enabled. This method of approach is repeated until the desired number of layers is achieved. Also, the first layer of vesicles may be immobilized by any of the methods known EP 0784793 and (Cooper and others 2000; Jung and others 2000; Patolsky and others 2000). The desired number of layers is dependant on the application.

In preferred embodiments of the Present invention, the vesicles 2 comprise an essentially spherical bilayer membrane structure of lipids, with lipid heads facing the exterior and the interior of the vesicle, forming a hydrophilic particle with a hydrophobic membrane layer and a hydrophilic interior. However, the vesicle could also comprise a essentially spherical monolayer of lipids with the hydrophilic lipid head facing the exterior of the vesicle forming a hydrophilic particle, and the lipid tails forming a hydrophobic interior of the vesicle (also known as micelles). The compounds forming the vesicle can be any compound capable of forming vesicles, or combination of such compounds. Such compounds can, among others, be phospholipids, sphingomyelin, cholesterol, plasmatogens and cardiolipids, but may also be compounds wherein the lipids forming the vesicles are linked to each other by polymerisation of the lipids themselves. In a preferred embodiment, the vesicles median size is in the range 5 nm to 10 µm, more preferably 25 nm to 150 nm. The conditions (buffer composition, pH, temperature, reaction rates etc) under which the production of a surface-immobilised multilayer structure of a plurality of vesicles according to the present invention takes place is dependent on a variety of factors, such as choice of surface material, vesicle composition, oligonucleotide sequences, etc. The conditions suitable for the different steps can easily be determined by a person skilled in the art. Examples of experimental conditions follow later, when a number of experiments performed are described.

In a preferred embodiment of the invention, vesicles 2 designed to form more than one layer vesicles are incubated with the surface 1 simultaneously, with the aim of forming said surface-immobilised multilayer structure in a single incubation step.

In another preferred embodiment of the invention, vesicles 2 designed to form a single layer of vesicles are incubated with the surface 1, with the aim of forming each layer of vesicles of said surface-immobilised multilayer structure in separate sequential incubation steps.

In a number of preferred embodiment of the present invention, the vesicles forming the surface-immobilised multilayer structure also comprises biologically active compounds 6, such as, but not limited to, membrane proteins, antibodies, functionalised lipids, coupled water soluble proteins etc. In an especially preferred embodiment of the present invention, the multilayer structure according to the invention is designed to be used for studies of the interactions between said biologically active compounds 6 incorporated in the vesicles 2 and analytes 7. Such studies includes, but are not limited to, antibody-antigen interactions, drug-target interaction and protein-binding interactions.

In other embodiments, the vesicles 2 may enclose different compounds, such as drugs, dyes, proteins, peptides, oligonucleotides and ions, etc in the interior 8 of the vesicle. The vesicles 2 may be designed in a way that these compounds may be released from the vesicles. This release may be triggered by an applied electrical potential, osmotic stress or incubation with a compound which stimulates said release. Said release may among other uses, be used in studies of localised drug delivery.

Different vesicles 2 may, by attaching different linkers 5 to different vesicles, be designed to be comprised in different layers to of the multilayer structure according to the present invention. Said different vesicles may comprise different biologically active compounds 6, thus designating different biological activity to different layers in the multilayer structure.

In specific embodiments, the invention relates to a multilayer structure of a plurality of vesicles 2 which can be immobilized to a surface 1, and additionally is designed to be released from the surface when triggered to do so. The release may be triggered by an applied electrical potential, osmotic stress, altered temperature or incubation with a compound Which stimulates said release.

In an especially preferred embodiment of the invention, said surface-immobilised multilayer structure of a plurality of vesicles is immobilised on a surface suitable for uses in biosensors. So the type of suitable surface is different for different biosensors, as described above.

In a further preferred embodiment of the invention, the formation of the surface-immobilised multilayer structure of a plurality of vesicles according to the present invention is performed in a biosensor and is monitored by a technique which detects the formation of said structure, and in a further preferred embodiment, any further studies on the properties of the said structure are performed in said biosensor.

It is to be understood that the above-mentioned embodiments and the following experiments are non-limiting examples of the present invention, and that the present invention also comprises other embodiments.

EXPERIMENTAL AND RESULTS

A plurality of lipid vesicles and proteoliposomes have been immobilized on a solid substrate utilizing subsequent hybridisation between complementary DNA-modified lipid vesicles. The preparation was analysed with surface plasmon resonance (SPR). The surface preparation was based on biotinylated albumin adsorbed on gold (surface coverage 90 ng/cm$^2$ (1440 RU)) followed by neutravidin (surface coverage 130 ng/cm$^2$ (2020 RU)), being in good agreement with previous results on similar systems (Jung and others 1998; Jung and others 2000; Svedhem and others 2003. Biotinylated DNA (bio-DNA) was then coupled to neutravidin (surface coverage 17 ng/cm$^2$ (260 RU)), demonstrating coupling of single-stranded DNA. The lipid vesicles or proteoliposomes, carrying single-stranded DNA complementary to the surface-immobilized DNA, were then exposed to the surface. A plurality of layers where created by subsequent exposures of liposomes or proteoliposomes carrying single stranded DNA being complementary to non-reacted DNA present of the vesicles in the outer most layer on the surfaces (see FIG. 3).

EXPERIMENTAL DETAILS

Protein and Protein assays: The membrane protein used to probe the signal enhancement of this multilayer system is the proton-translocating-nicotinamide-nucleotide Transhydrogenase (TH) from the bacterium *Escherichia Coli*. (Meuller and others 1997) To verify the enhancement in signal, several layers of vesicles are compared with one layer of vesicles and ⅓ of the protein was cleaved off from the rest of the protein by trypsin treatment, (Tong and Others 1991) leading to a decreased signal in the SPR measurements e.g. decreased mass within the field sensed by SPR.

Figure 3:
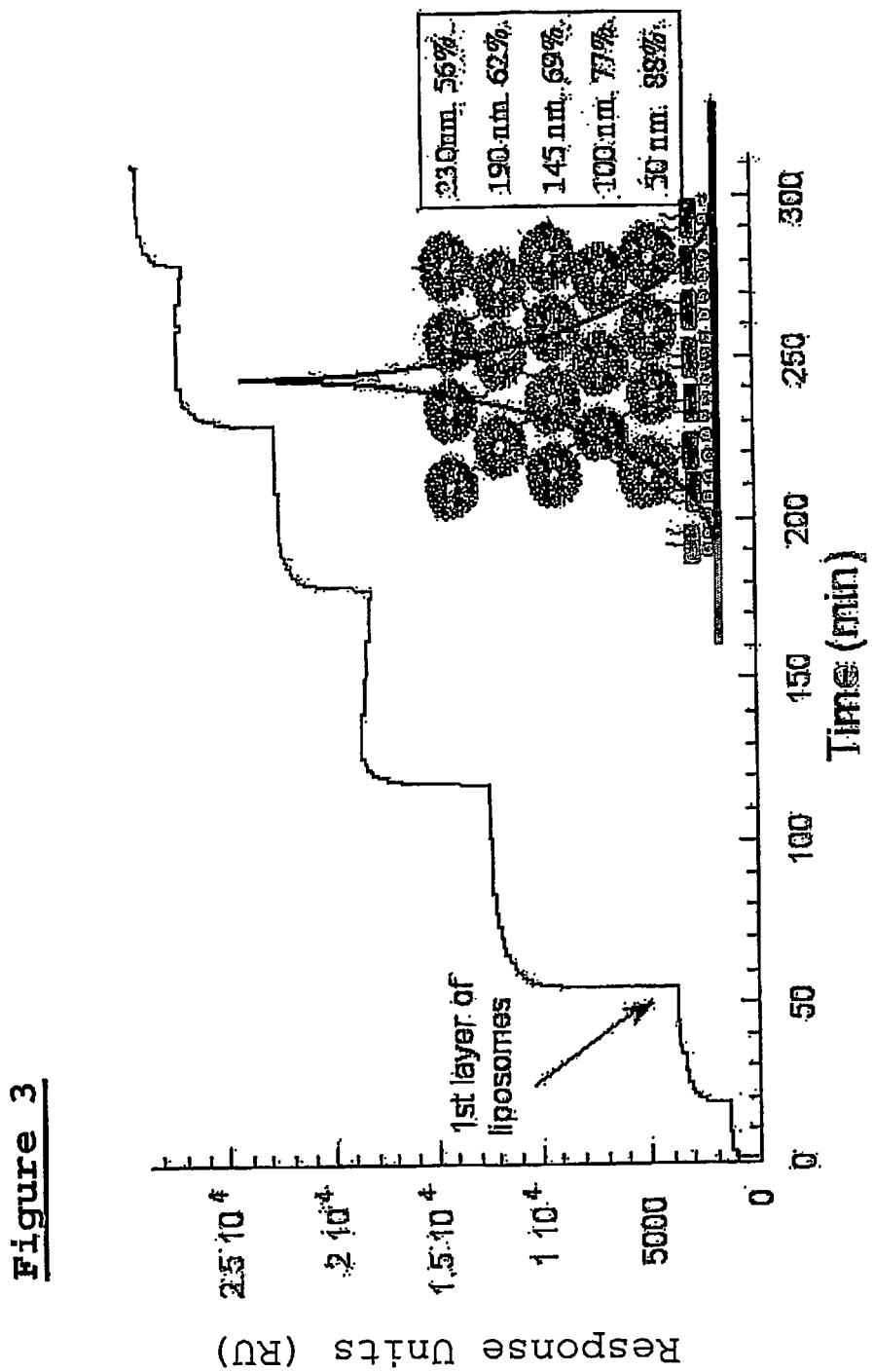
FIG. 3 shows the measured response units (MRU) in which the SPR-results of the multilayer preparation. The thickness of the layers and the percentage of the response that is sensed by the evanescent wave are also shown. Five layers of liposomes were immobilized on the surface.
Figure 4:
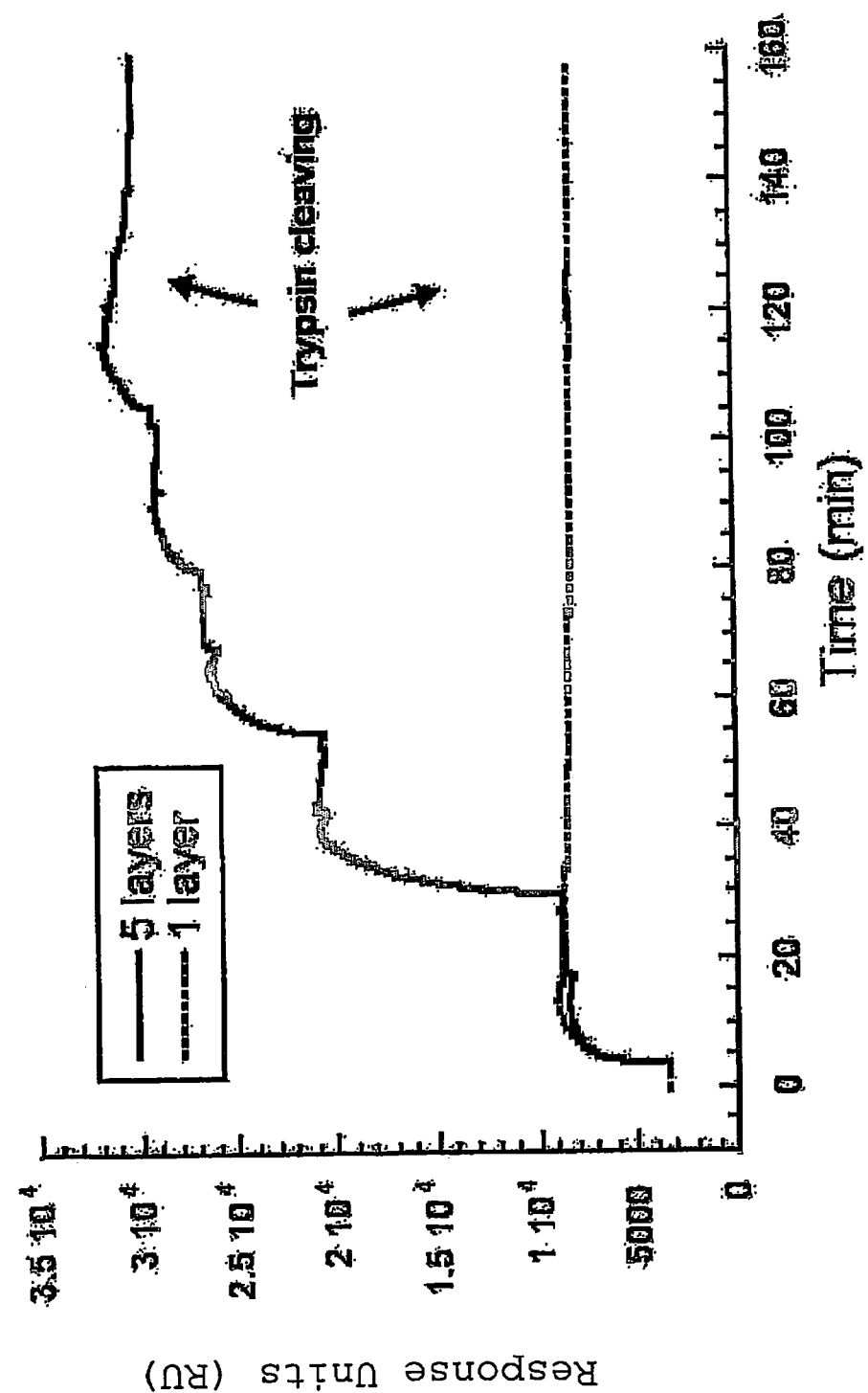
FIG. 4 shows the immobilization of one and five layers of TH-containing proteoliposomes. After immobilization of the proteoliposomes, trypsin is added to cleave the TH, resulting in a mass loss from the surface.

Lipids, Liposomes and Proteoliposomes: The liposomes (FIG. 3) consist of the lipid phosphatidylcholine and the proteoliposomes (FIG. 4) consist of the lipids phosphatidylethanolamine, phosphatidylcholine and phosphatidylserine in a composition of 50%-45%-5%. Liposomes were made either from extrusion (FIG. 3) through a 100 nm filter or by sonic-rod sonication (~30 min) followed by centrifugation of the solution to remove larger lipid entities (FIG. 4). The liposomes formed by extrusion have a diameter of 130-150 nm and the sonicated liposomes are 25 nm in diameter. Single stranded cholesterol-DNA (chol-DNA) was incorporated into the liposomes during the extrusion and sonication process. The different DNA-strands are referred to as DNA or c-DNA (complementary DNA-strand). The membrane protein TH was incorporated into the sonicated liposomes by detergent mediated reconstitution. (Granèli and others 2003; Meuller and others 1997; Richard and others 1990)

The surface preparation: The gold surfaces were cleaned in between different measurements in SDS and uv-ozone treatment.

The multilayer preparation: Liposomes or proteoliposomes functionalised with c-DNA were exposed to the bio-DNA modified surface. After saturated binding, additional chol-c-DNA was added to the immobilized liposomes. Liposomes, functionalised with chol-DNA, were then exposed to the surface. After saturated binding, the process was repeated, but with addition of chol-DNA and subsequent addition of vesicles modified with chol-c-DNA). These sequences were then repeated until five layers of liposomes were immobilized.

Surface Plasmon Resonance (SPR): The Surface Plasmon Resonance measurements were performed on a Biacore 2000 (Biacore AB, Uppsala, Sweden).

Results

SPR-Results on immobilization of multilayers of liposomes on a gold surface: The immobilisation of liposomes in the multilayer was measured using SPR as shown in FIG. 3. The evanescent wave associated with the surface plasmon, also determining the sensitivity of SPR vs distance from the surface, is described follows an exponential behaviour with a decay length of approximately 400 nm, as schematically illustrated in FIG. 3. Taking the decrease in the volume sensed by the evanescent wave as the distance from the surface increases into account, the measured response units (AMRU) can be converted into the real response units (ARRU) by equation 1. (Liedberg and others 1993)

$$\Delta RRU = \Delta MRU \times e^{z/dZ} \quad (1)$$

where z is the thickness of the adsorbed layer (evaluated using QCM-D (see inset in FIG. 3), and dz is the decay-length of the evanescent field, being 400 nm in this case.

When using Eq.1 and the AMRU shown in FIG. 3 the mass of the adsorbed lipid can be determined by using Eq. 2.

$$\Delta m = C \times \Delta RRU \quad (2)$$

where $\Delta m$ is the coupled mass and C is the mass (ng) per $c^2$ that corresponds to a change of $\Delta RRU$ of 1. C has been determined for proteins to be 0.066 ng/cm$^2$ and for lipids 0.059 ng/cm$^2$ by using the refraction index for the different molecules. (Liedberg and others 1993) The calculated values of the lipid mass adsorbed on the surface are shown in Table 1.

TABLE 1

Table 1. The calculated value of ΔRRU and the mass of the lipids in each liposome-layer.

| Layer number | ΔRRU | Lipid mass (ng/cm$^2$) |
|---|---|---|
| 1 | 10370 | 612 |
| 2 | 9340 | 551 |
| 3 | 9170 | 541 |
| 4 | 10870 | 641 |
| 5 | 8170 | 482 |

The results presented in Table 1 demonstrate that each layer is composed of essentially the same amount of lipid vesicles, despite the fact that AMRU decreases as the distance from the surface increases (FIG. 3). Thus, the presented strategy to create a plurality of lipid vesicles in a multilayer structure based on complementary DNA is efficient and not expected to be limited to only a few layers.

A multilayer structure of TH-containing proteoliposomes including trypsin cleavage of TH: A multilayer of proteoliposomes was immobilized on the gold-surface as described above. The SPR-results of the immobilization process is shown in FIG. 4. Also shown is the creation of a single layer of proteoliposomes. Trypsin cleavage of TH, during which a 43 kD domain of the protein is removed, was done after saturated formation of five and one layer of liposomes, respectively.

Figure 5:
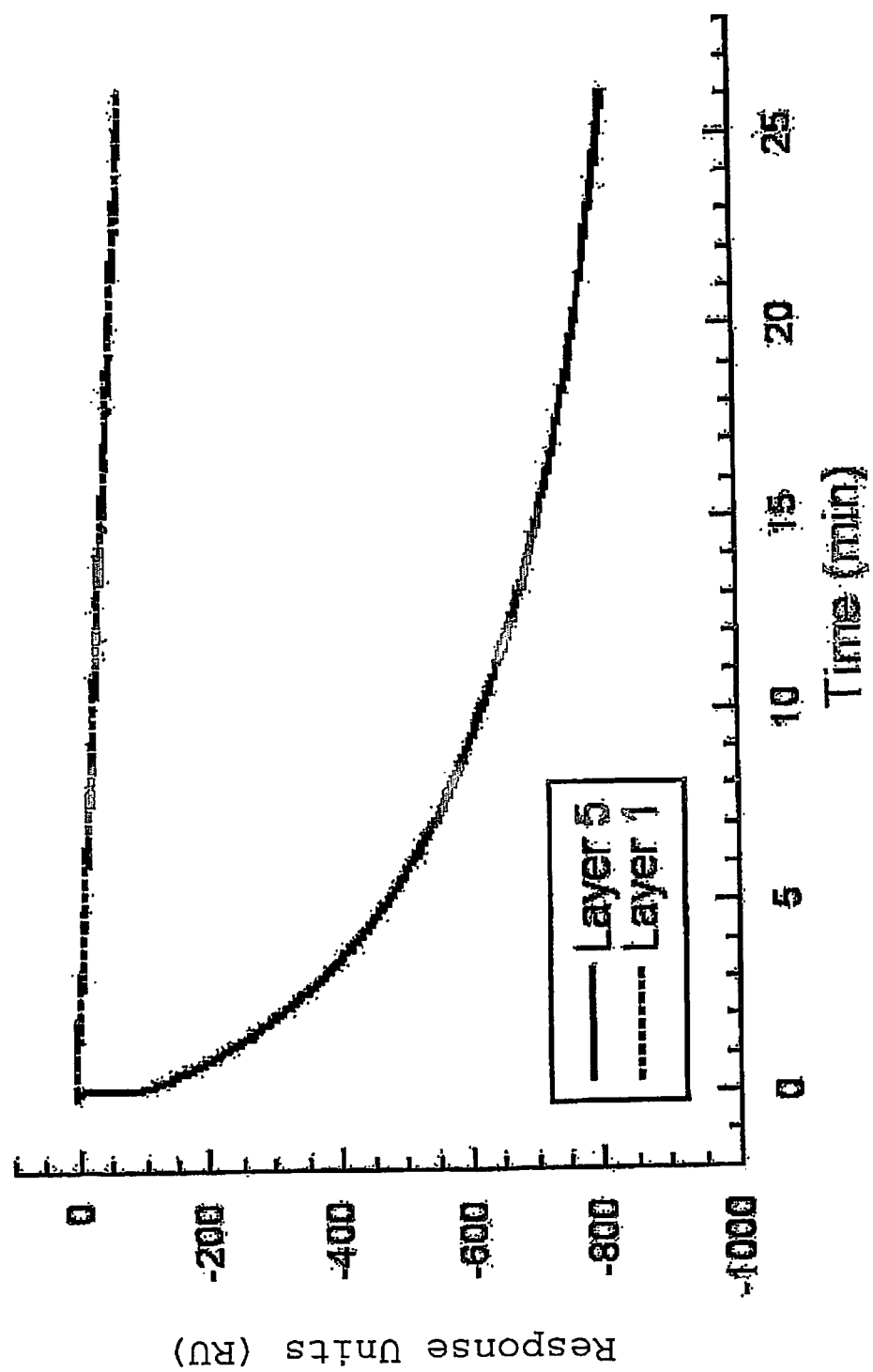
FIG. 5 shows a close-up of the trypsin cleavage of TH in one or five layers of proteoliposomes in FIG. 4.
Figure 6:
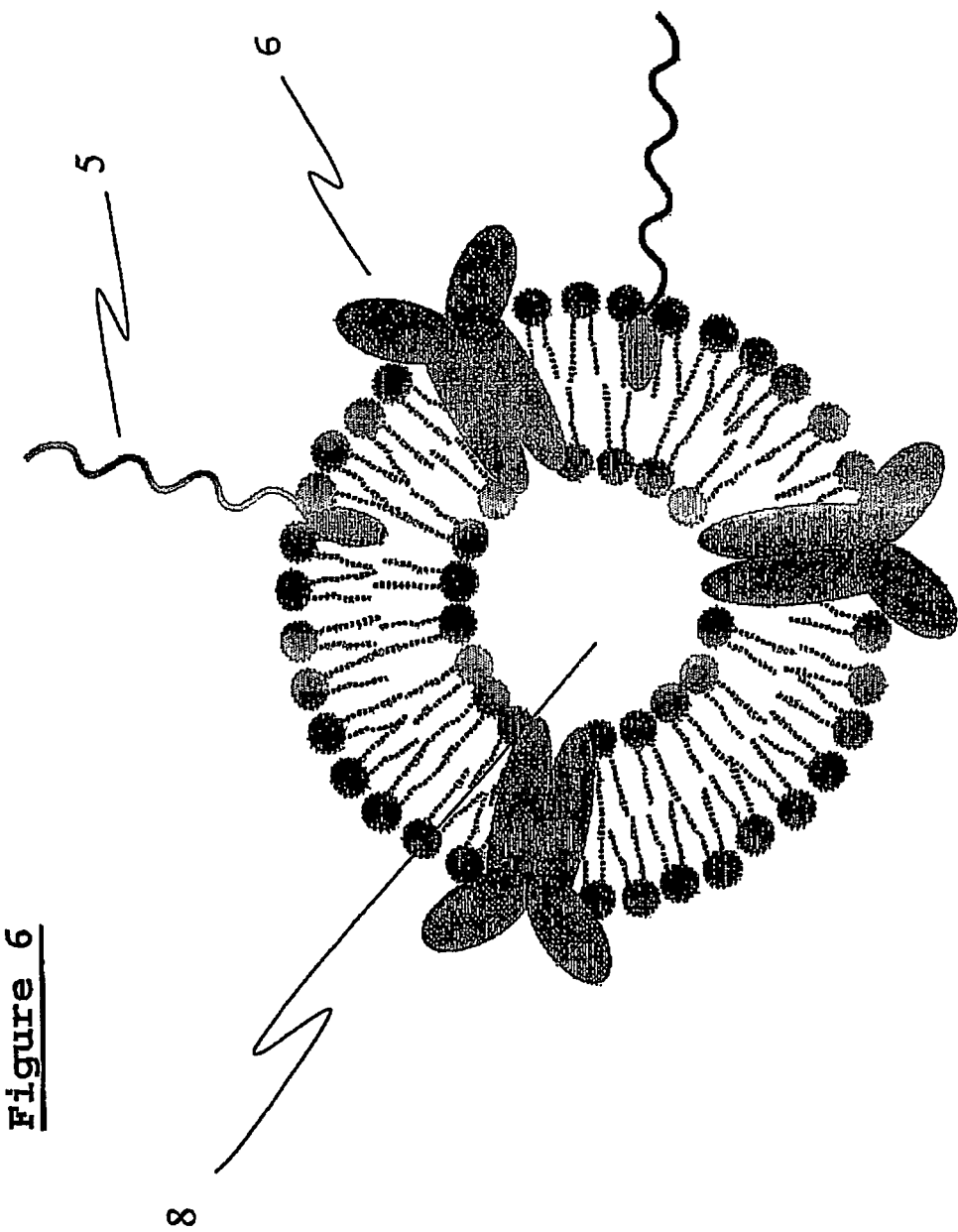
FIG. 6 shows a vesicle 2 with linkers 5 attached to the vesicle, and with biologically active compounds 6 embedded in the lipid bilayer forming the vesicle, the figure also showing the interior volume 8 of the vesicle.

FIG. 5, shows a magnification of the trypsin cleavage step for five and one layer of vesicles, nicely demonstrating that the multilayer structure, which carries significantly more TH, gives a significantly larger response than that of a single layer of vesicles. The observed amplification is in fact larger than expected, signalling that the membrane protein TH in the first layer of vesicles is in fact influenced by the underlying surface, an effect which is reduced as the distance from the surface increases.

REFERENCES

Brian A A, McConnell H M. 1984. Allogenic stimulation of cytotoxic T cells by supported planar membranes. Proc. Natl. Acad. Sci. 81(19):6159-6163.

Burgess J D, Rhoten M C, Hawkridge F M. 1998. Cytochrome c Oxidase Immobilized in Stable Supported Lipid Bilayer Membranes. Langmuir 14:2467-2475.

Cooper M A, Hansson A, Löfås S, Williams D H. 2000. A vesicle Capture Sensor Chip for Kinetic Analysis of Interactions with Membrane-Bound Receptors. Analytical Chemistry 277:196-205.

Gizeli E, Liley M, Lowe C R, Vogel R. 1997. Antibody binding to a Functionalized Supported Lipid Layer: A direct Acoustic Immunosensor. Analytical Chemistry 69:4808-4813.

Granèli A, Rydström J, Kasemo B, Höök F. 2003. Formation of supported lipid bilayer membranes on SiO2 from proteoliposomes containing transmembrane proteins. Langmuir 19:842-850.

Gritsch S, Nollert P, Jahnig F, Sackmann E. 1998. Impedance Spectroscopy of Porin and Gramicidin Pores Reconstituted into Supported Lipid Bilayers on Indium-Tin-Oxide Electrodes. Langmuir 14(11):3118-3125.

Gronow M. 1984. Biosensors. Trends in Biochemical Sciences 9(8):336-340.

Heyse S, Ernst O P, Dienes Z, Hofmann K P, Vogel A. 1998. Incorporation of Rhodopsin in Laterally structured Supported Membranes: Observations of Transducin Activation with Spatially and Time-Resolved Surface Plasmon Resonance. Biochemistry 37:507-522.

Janshoff A, Galla H J, Steinem C. 2000. Piezoelectric mass-sensing devices as biosensors—An alternative to optical biosensors? Angewandte Chemie-International Edition 39(22):4004-4032.

Jordan C E, Frutos A G, Thiel A J, Corn R M. 1997. Surface plasmon resonance imaging measurements of DNA hybridization adsorption and streptavidin/DNA multilayer formation at chemically modified gold surfaces. Analytical Chemistry 69(24):4939-4947.

Jung L S, Campbell C T, Chinowsky T M, Mar M N, Yee S S. 1998. Quantitative Interpretation of the Response of Surface Plasmon Resonance Sensors to Adsorbed Films. Langmuir 14:5636-5648.

Jung L S, Shumaker-Perry J S, Campbell C T, Yee S S, Gelb M H. 2000. Quantification of Tight Binding to Surface-Immobilized Phospholipid Vesicles Using Surface Plasmon Resonance: Binding Constant of Phospholipase $A_2$. J. Am. Chem. Soc. 122:4177-4184.

Kalb E, Tamm L K. 1992. Incorporation of cytochrome b5 into supported phospholipid bilayers by vesicle fusion to supported monolayers. Thin Solid Films 210/211:763-765.

Karlsson O P, Lofas S. 2002. Rapid on-surface reconstitution of GPCR for applications in SPR biosensors. Biophysical Journal 82 (1):1053.

Karlsson O P, Löfås S. 2002. Flow-Mediated On-Surface Reconstitution of G-Protein Coupled Receptors for Applications in Surface Plasmon Resonance Biosensor. Analytical Biochemistry 300:132-138.

Keller C A, Kasemo B. 1998. Surface specific kinetics of lipid vesicle adsorption measured with a quartz crystal microbalance. Biophysical Journal 75(3):1397-1402.

Lieberman T, Knoll W. 2000. Surface-plasmon field-enhanced fluorescence spectroscopy. Colloids and Surfaces a-Physicochemical and Engineering Aspects 171(1-3):115-130.

Liedberg B, Lundström I, Stenberg E. 1993. Principles of biosensing with an extended coupling matrix and surface plasmon resonance. 11:63-72.

Lindholm-Sethson B, Carrasco Gonzalez, Juan Puu, Gertrud. 1998. Electron Transfer to a Gold Electrode from Cytochrome Oxidase in a Biomembrane via a Polyelectrolyte Film. Langmuir 14 (23):6705-6708.

MacKenzie C R, Hirama T, Lee K K, Altman E, Young N M. 1997. Quantitative analysis of bacterial toxin affinity and specificity for glycolipid receptors by surface plasmon resonance. Journal of Biological Chemistry 272(9):5533-5538.

Meuller J, Zhang J, Hou C, Bragg P, Rydström J. 1997. Properties of the cysteine-free proton-pumping nicotinamide nucleotide transhydrogenase. Biochemical Journal 324:681-687.

Michel R, Reviakine I, Sutherland D, Fokas C, Csucs G, Danuser G, Spencer N D, Textor M. 2002. A novel approach to produce biologically relevant chemical patterns at the nanometer scale: Selective molecular assembly patterning combined with colloidal lithography. Langmuir 18(22):8580-8586.

Naumann r, Baumgart T, Gräber P, Jonczyk A, Offenhäuser A, Knoll W. 2002. Proton transport through a peptide-tethered bilayer lipid membrane by the $H^+$-ATP synthase from chloroplasts measured by impedance spectroscopy. Biosensors and Bioelectronics 17:25-34.

Niemeyer C M, Blohm D. 1999. DNA microarrays. Angewandte Chemie-International Edition 38(19):2865-2869.

Patolsky F, Lichtenstein A, Willner I. 2000. Amplified microgravimetric quartz-crystal-microbalance assay of DNA using oligonucleotide-functionalized liposomes or biotinylated liposomes. Journal of the American Chemical Society 122(2):418-419.

Ramsden J J. 1993. Review of New Experimental-Techniques For Investigating Random Sequential Adsorption. Journal of Statistical Physics 73(5-6):853-877.

Reimhult E, Hook F, Kasemo B. 2002. Vesicle adsorption on SiO2 and TiO2: Dependence on vesicle size. Journal of Chemical Physics 117(16):7401-7404.

Rich R L, Myszka D G. 2000. Survey of the 1999 surface plasmon resonance biosensor literature. Journal of Molecular Recognition 13(6):388-407.

Richard P, Rigaud J-L, Gräber P. 1990. Reconstitution of CF0F1 into liposomes using a new reconstitution procedure. Eur. J. Biochem 193:921-925.

Salafsky J, Groves J T, Boxer S G. 1996. Architecture and function of Membrane Proteins in Planar Supported Bilayers: A Study with Photosynthetic Reaction Centers. Biochemistry 35:14773-14781.

Schmidt C, Mayer M, Vogel H. 2000. A chip-based biosensor for the functional analysis of single ion channels. Angewandte Chemie-International Edition 39(17):3137-3140.

Svedhem S, Pfeiffer I, Larsson C, Wingren C, Borrebaeck C, Hook F. 2003. Patterns of DNA labelled and ScFv—antibody carrying lipid vesicles directed by material specific immobilization of DNA and supported lipid bilayer formation on an Au/SiO2 template. ChemBioChem 4(4):339-343.

Tong R C W, Glavas N A, Bragg P D. 1991. Topological analysis of the pyridine nucleotode transhydrogenase of *Escherichia coli* using proteolytic enzymes. biochimica et Biophysica Acta 1080:19-28.

Wagner M L, Tam L K. 2000. Tethered Polymer-Supported Planar Lipid Bilayers for Reconstitution of Integral Membrane Proteins: Silane-Polyethyleneglycol-Lipid as a Cushion and Covalent Linker. Biophysical Journal 79:1400-1414.

Zacher T. Wischerhoff E. 2002. Real-Time Two-Wavelength Surface Plasmon Resonance as a Tool for the Vertical Resolution of Binding Processes in Biosensing Hydrogels. Langmuir 18:1748-1759.

The invention claimed is:

1. A biologically-functional, surface-immobilized multilayer structure, comprising (i) a support surface, (ii) a plurality of first vesicles formed of a lipid bilayer membrane and spaced apart from said surface, and (iii) a plurality of second vesicles formed of a lipid bilayer membrane and spaced apart from said surface,
   wherein the plurality of first vesicles is directly attached to the surface by binding surface-immobilized linkers with vesicle-attached linkers to form a first immobilized layer of the plurality of first vesicles,
   wherein the plurality of the second vesicles is attached to the first immobilized layer of the plurality of first vesicles by binding vesicle-attached linkers to vesicle-attached linkers to form two or more immobilized layers of the plurality of second vesicles,
   wherein the surface-immobilized linkers and the vesicle-attached linkers comprise oligonucleotides and binding of one linker to another linker is mediated through hybridization of said linker oligonucleotides; and
   wherein at least a selected population of said vesicles comprise a biologically active compound which provides the structure with biological functionality.

2. A structure according to claim 1, wherein said vesicle-attached linkers are attached to said vesicles via at least one of a hydrophobic anchoring moiety comprised in said vesicle-attached linker and a covalent bond to said vesicle via a functionalised group comprised in said vesicle-attached linker.

3. A structure according to claim 1, wherein said vesicles are coated with an outer shell comprising compounds selected from the group consisting of polyethylene glycol, S-layer proteins, peptides, metal clusters and polymers, or wherein vesicle lipids themselves are linked by polymerisation.

4. A structure according to claim 1, wherein the interior volume of said vesicles comprises compounds selected from the group consisting of ions, dyes, drugs, antibodies, enzymes and other proteins.

5. A structure according to claim 1, adapted for release of said multilayer structure from said surface.

6. A structure according to claim 5, designed so that said release is triggered by an electrical potential, light, osmotic stress or incubation with a compound which stimulates said release.

7. A structure according to claim 1, wherein at least two vesicles are attached to each surface-immobilized linker.

8. A structure according to claim 7, wherein said surface-immobilized linker comprises at least one non-linker attached region with a biological functionality.

9. A structure according to claim 8, wherein said non-linker attached region is capable of specific binding with an analyte.

10. A structure according to claim 7, wherein said vesicle-attached linkers are attached to said vesicles via at least one of a hydrophobic anchoring moiety comprised in said linker, and a covalent bond to said vesicle via a functionalised group comprised in said linker.

11. A structure according to claim 7, wherein said vesicles are coated with an outer shell comprising compounds selected from the group consisting of polyethylene glycol, S-layer proteins, peptides, metal clusters and polymers, or wherein vesicle lipids themselves are linked by polymerisation.

12. A structure according to claim 7, wherein the interior volume of said vesicles comprises compounds selected from the group consisting of ions, dyes, drugs, antibodies, enzymes and other proteins.

13. A structure according to claim 7, adapted for release of said multilayer structure from said surface.

14. A structure according to claim 13 designed so that said release is triggered by an electrical potential, light, osmotic stress or incubation with a compound, which stimulates said release.

15. A structure according to claim 1, wherein the vesicles comprise a biologically active compound selected from the group consisting of membrane proteins, antibodies, functionalized lipids, and coupled water-soluble proteins.

16. A structure according to claim 1, wherein the vesicles comprise biologically active membrane proteins.

17. A structure according to claim 1, wherein the vesicles comprise a biologically active compound selected from the group consisting of drugs, proteins, peptides, and oligonucleotides.

18. A method for producing a surface-immobilised multilayer structure according to claim 1, the method comprising the steps of: (i) providing a support surface comprising linkers immobilised onto the surface, each said surface-immobilised linker being adapted and available for binding to at least one vesicle-attached linker; (ii) providing vesicles formed of a lipid bilayer membrane, each vesicle comprising outwardly projecting linkers attached thereto, each said vesicle-attached linker being adapted and available for direct binding to a surface-immobilised linker or another vesicle-attached linker, (iii) incubating a first plurality of the vesicles with the surface under conditions promoting binding of vesicle-attached linker(s) directly to the surface-immobilised linker(s) to form a first immobilized layer of the first plurality of vesicles, and incubating at least a second plurality of the vesicles with the surface under conditions promoting binding of vesicle-attached linker(s) directly to the vesicle-attached linker(s) already immobilised, resulting in immobilisation of the second plurality of vesicle(s) and the linker(s) attached thereto to form two or more immobilized layers of the second plurality of vesicles, and (iv) repeating the previous step until the desired amount of vesicles are immobilised,
  wherein the surface-immobilized linkers and the vesicle-attached linkers comprise oligonucleotides and binding of one linker to another linker is mediated through hybridization of said linker oligonucleotides, and
  wherein at least a selected population of said vesicles comprise a biologically active compound which provides the structure with biological functionality.

19. A method according to claim 18, wherein said surface-immobilised linker comprises at least two sites for binding of vesicle-attached linkers.

20. A method according to claim 18, wherein said surface-immobilised linker comprises only one site for binding of vesicle-attached linkers.

21. A method according to claim 18, wherein said vesicle-attached linkers are attached to said vesicles via at least one of a hydrophobic anchoring moiety comprised in the linker, and a covalent bond to said vesicle via a functionalised group comprised in the linker.

22. A method according to claim 18, wherein said vesicles are coated with an outer shell comprising of compounds selected from the group consisting of polyethylene glycol, S-layer proteins, peptides, metal clusters and polymers.

23. A method according to claim 18, wherein the interior volume of said vesicles comprises compounds selected from the group consisting of ions, dyes, drugs, antibodies, enzymes and other proteins.

24. A method according to claim 18, wherein said surface comprises several surface-immobilised vesicles, which serves as a binding matrix for said structure.

25. A method according to claim 18, wherein said incubation is performed under conditions promoting sequence specific hybridisation of said oligonucleotides.

26. A method according to claim 18, also comprising the step of releasing compounds from the vesicles.

27. A method according to claim 26, wherein said release is triggered by an applied electrical potential osmotic stress or incubation with a compound, which stimulates said release.

28. A method for producing a multilayer structure of a plurality of vesicles, comprising the method according to claim 18, followed by the step of releasing said multilayer structure from said surface.

29. A method according to claim 28, wherein said release is triggered by an electrical potential, osmotic stress or incubation with a compound, which stimulates said release.

30. A biosensor, comprising a structure according to claim 1.

31. A biosensor, comprising a structure produced according to claim 18.

32. The biosensor according to claim 30, wherein said biosensor is an optical biosensor, and said structure is used for increasing the signal of said optical biosensor.

33. The biosensor according to claim 30, wherein said biosensor is a mechanical biosensor, and said structure increases a signal of said mechanical biosensor.

* * * * *